(12) United States Patent
Weiman et al.

(10) Patent No.: US 8,968,363 B2
(45) Date of Patent: Mar. 3, 2015

(54) TISSUE RETRACTOR AND METHODS OF USE

(75) Inventors: Mark Weiman, Coatesville, PA (US); Jason Cianfrani, East Norriton, PA (US)

(73) Assignee: Globus Medical, Inc., Audubon, PA (US)

(\*) Notice: Subject to any disclaimer, the term of this patent is extended or adjusted under 35 U.S.C. 154(b) by 377 days.

(21) Appl. No.: 13/049,701

(22) Filed: Mar. 16, 2011

(65) Prior Publication Data

US 2011/0224497 A1    Sep. 15, 2011

Related U.S. Application Data

(63) Continuation-in-part of application No. 12/722,100, filed on Mar. 11, 2010, now Pat. No. 8,353,826.

(51) Int. Cl.
| | | |
|---|---|---|
| *A61B 1/32* | (2006.01) | |
| *A61B 17/02* | (2006.01) | |
| *A61B 19/00* | (2006.01) | |

(52) U.S. Cl.
CPC ............. *A61B 17/0206* (2013.01); *A61B 17/02* (2013.01); *A61B 19/26* (2013.01)
USPC ........................................................ 606/231

(58) Field of Classification Search
CPC .................................. A61B 1/32; A61B 19/26
USPC .................................................. 600/201–246
See application file for complete search history.

(56) References Cited

U.S. PATENT DOCUMENTS

| | | |
|---|---|---|
| 5,067,477 A | 11/1991 | Santangelo |
| 5,795,291 A | 8/1998 | Koros et al. |
| 5,928,139 A | 7/1999 | Koros et al. |
| 5,931,777 A | 8/1999 | Sava |
| 5,944,658 A | 8/1999 | Koros et al. |
| 6,074,343 A | 6/2000 | Nathanson et al. |
| 6,083,154 A | 7/2000 | Liu et al. |
| 6,322,500 B1 | 11/2001 | Sikora et al. |
| 6,416,470 B2 | 7/2002 | Paolitto et al. |
| 6,464,634 B1 | 10/2002 | Fraser |
| 6,712,795 B1 | 3/2004 | Cohen |
| 6,869,398 B2 | 3/2005 | Obenchain et al. |
| 7,195,592 B2 | 3/2007 | Ravikumar et al. |
| 7,344,495 B2 | 3/2008 | Ravikumar et al. |
| 7,537,565 B2 | 5/2009 | Bass |
| 7,556,600 B2 | 7/2009 | Landry et al. |
| 7,618,367 B2 | 11/2009 | Martin et al. |

(Continued)

FOREIGN PATENT DOCUMENTS

EP    1829488 A1    9/2007

OTHER PUBLICATIONS

International Search Report and Written Opinion in related matter PCT/US12/29539 mailed Jul. 13, 2012.

(Continued)

*Primary Examiner* — Christopher Beccia

(57) ABSTRACT

Methods and devices for retracting tissue in a surgical procedure to allow access to the surgical site. Retractor systems and methods that comprise a retractor frame comprising rotatable arms and a linearly translatable arm, the rotatable arms and the linearly translatable arm each coupled to blades that can angulate. Systems for securing a retractor system to a patient's spine, the systems comprising a retractor blade and a shim device.

6 Claims, 14 Drawing Sheets

(56) References Cited

U.S. PATENT DOCUMENTS

| | | |
|---|---|---|
| 7,850,608 B2 | 12/2010 | Hamada |
| 7,976,463 B2 | 7/2011 | Dewey et al. |
| 2005/0137461 A1* | 6/2005 | Marchek et al. ............... 600/220 |
| 2005/0215863 A1 | 9/2005 | Ravikumar et al. |
| 2006/0074278 A1 | 4/2006 | Petit et al. |
| 2006/0224044 A1 | 10/2006 | Marchek et al. |
| 2007/0021656 A1 | 1/2007 | Martin et al. |
| 2007/0038033 A1 | 2/2007 | Jones et al. |
| 2007/0073111 A1 | 3/2007 | Bass |
| 2007/0073112 A1 | 3/2007 | Holmes |
| 2007/0100212 A1* | 5/2007 | Pimenta et al. ............... 600/210 |
| 2007/0123753 A1 | 5/2007 | Abdelgany |
| 2007/0156025 A1 | 7/2007 | Marchek et al. |
| 2007/0156026 A1 | 7/2007 | Frasier et al. |
| 2007/0208228 A1 | 9/2007 | Pavento et al. |
| 2007/0238932 A1 | 10/2007 | Jones et al. |
| 2007/0282171 A1 | 12/2007 | Karpowicz et al. |
| 2007/0293729 A1* | 12/2007 | Grey et al. ................... 600/212 |
| 2008/0058605 A1 | 3/2008 | Sorensen |
| 2008/0114208 A1 | 5/2008 | Hutton |
| 2008/0114209 A1 | 5/2008 | Cohen et al. |
| 2008/0183046 A1* | 7/2008 | Boucher et al. ............... 600/232 |
| 2008/0188718 A1 | 8/2008 | Spitler et al. |
| 2008/0249372 A1 | 10/2008 | Reglos et al. |
| 2009/0018401 A1 | 1/2009 | Kim |
| 2009/0069635 A1 | 3/2009 | Gephart et al. |
| 2009/0076516 A1 | 3/2009 | Lowry et al. |
| 2009/0124861 A1 | 5/2009 | Fetzer |
| 2009/0203969 A1 | 8/2009 | Cohen et al. |
| 2009/0227845 A1 | 9/2009 | Lo et al. |
| 2010/0113885 A1 | 5/2010 | McBride et al. |
| 2010/0152603 A1 | 6/2010 | Miles et al. |

OTHER PUBLICATIONS

International Search Report and Written Opinion in related matter PCT/US11/28008 mailed May 25, 2011.

IPRP in related matter PCT/US11/28008.

* cited by examiner

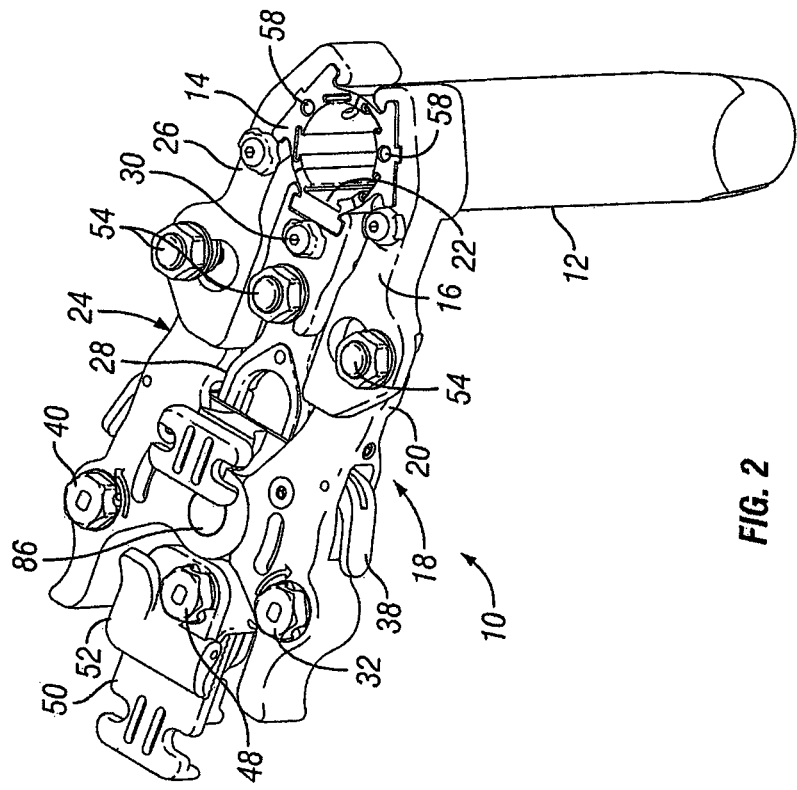
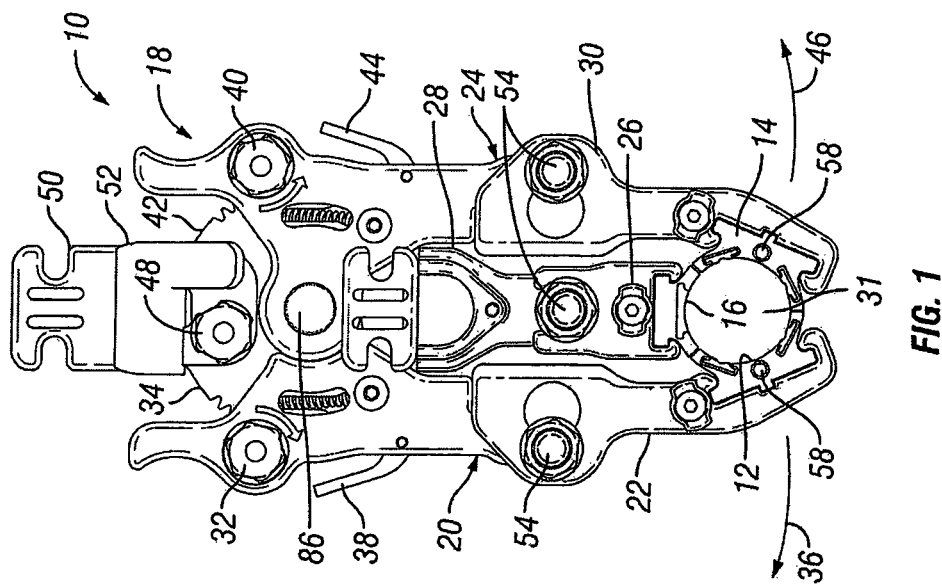

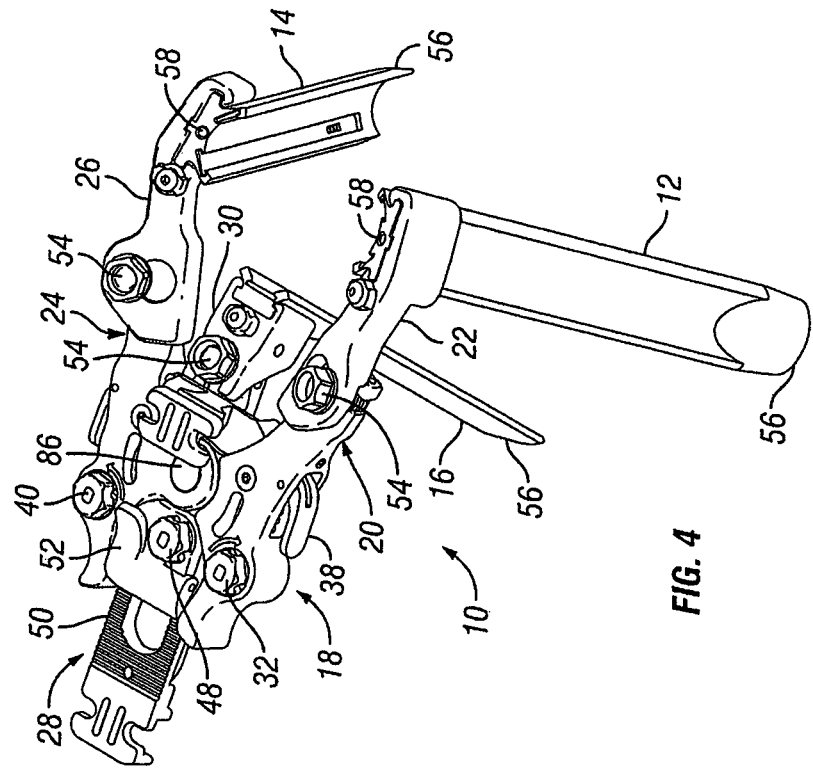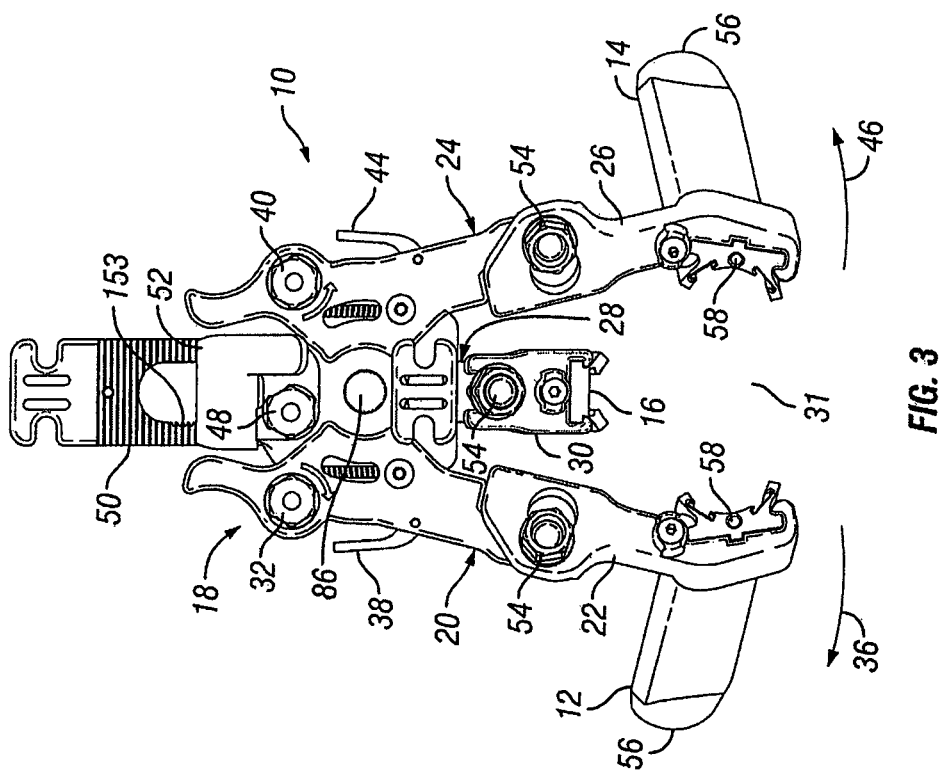

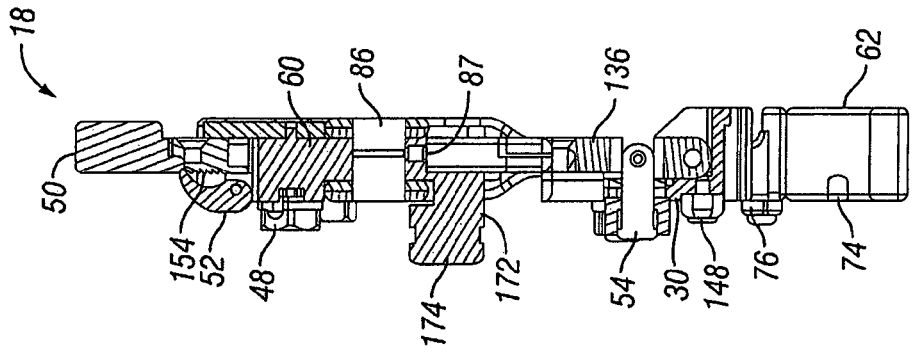
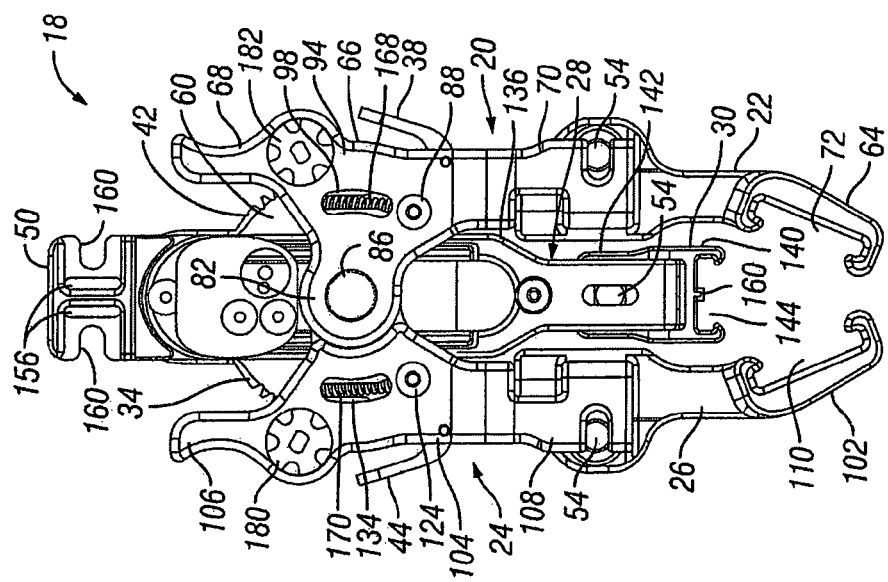

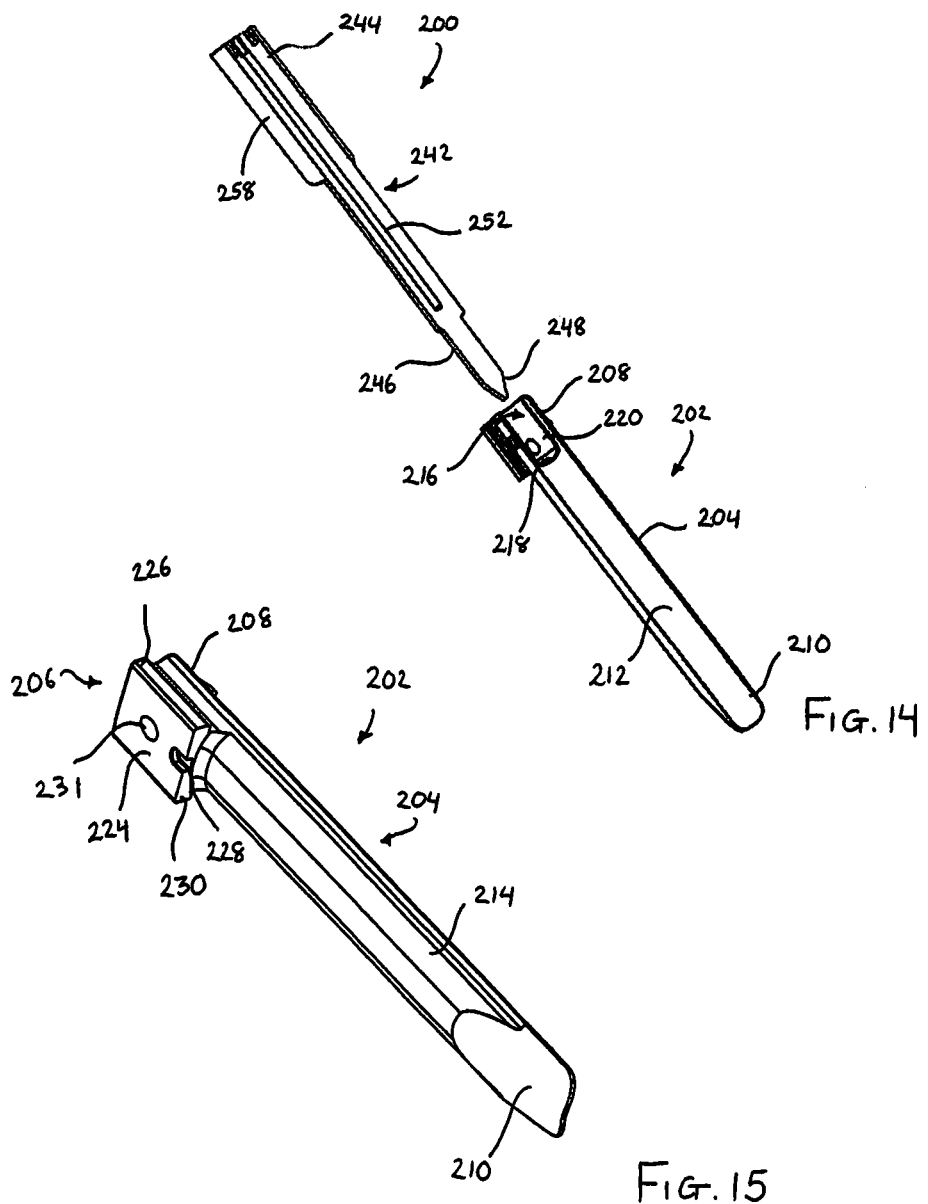

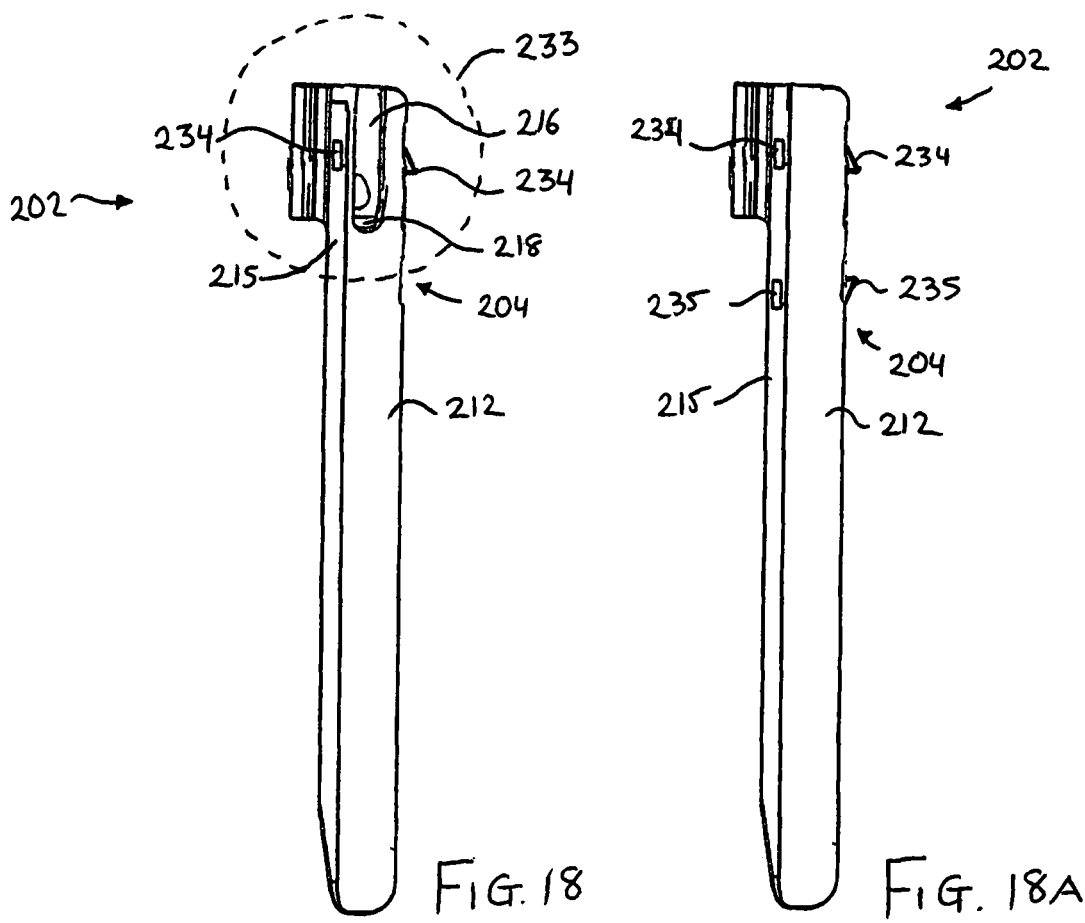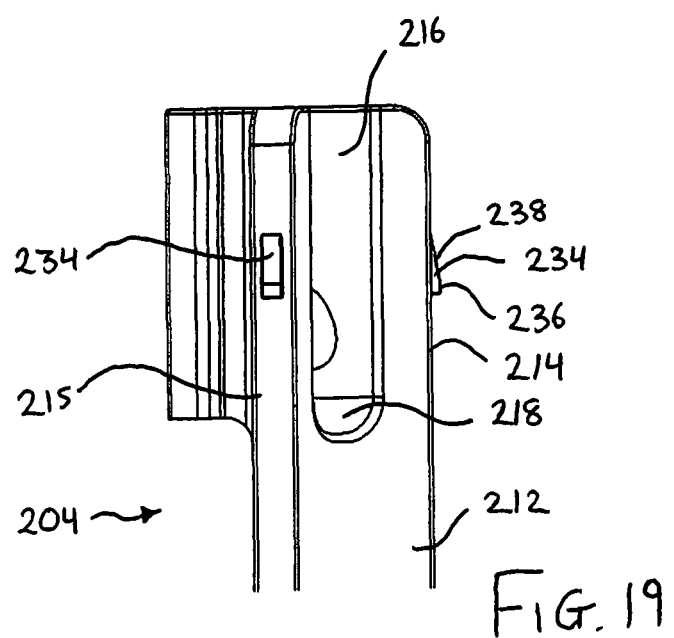

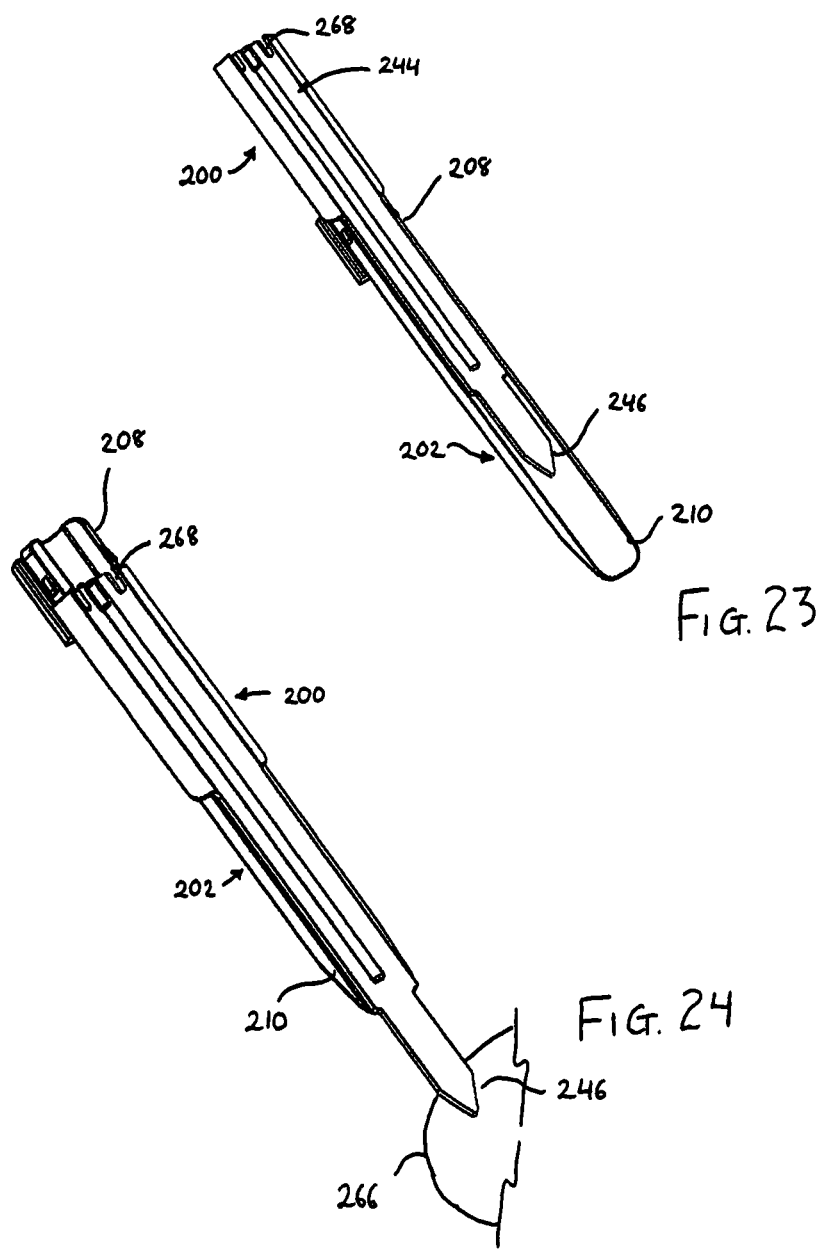

TISSUE RETRACTOR AND METHODS OF USE

CROSS-REFERENCE TO RELATED APPLICATIONS

The present application is a continuation in part of U.S. application Ser. No. 12/722,100, entitled "Tissue Retractor and Methods of Uses," filed on Mar. 11, 2010, now U.S. Pat. No. 8,353,826 the disclosure of which is incorporated herein by reference.

FIELD OF THE INVENTION

The present disclosure generally relates to medical devices. In particular, in one or more embodiments, the present disclosure relates to methods and devices for retracting tissue in a surgical procedure to allow access to the surgical site.

BACKGROUND

Retractor systems may be used in a variety of different surgical procedures to provide an opening through which the doctor may access the surgical site. In spinal surgeries, for example, a retractor system may be used to provide the surgeon with access to the patient's spine. The opening created by the retractor system may, for example, enable the doctor to insert surgical instruments into the body or enable visualization of the surgical site using X-ray. One typical retractor system may include a plurality of blades coupled to a retractor frame. In use, the blades may be inserted into an incision and then retracted to displace tissue surrounding the incision down to the surgical site. To minimize trauma to the tissue, this tissue displacement should generally be refined and controlled. However, current retractor systems may not provide desired control of the distraction.

Thus, there is a need for improved methods and devices that can be used for retracting tissue to provide access to the surgical site.

SUMMARY

The present disclosure generally relates to medical devices. In particular, in one or more embodiments, the present disclosure relates to methods and devices for retracting tissue in a surgical procedure to allow access to the surgical site.

An embodiment may comprise a retractor system. The retractor system may comprise a retractor frame. The retractor frame may comprise a first rotatable arm, a second rotatable arm, and a linearly translatable arm coupled to the first and second rotatable arms. The first blade may be coupled to a distal end of the first rotatable arm. The first rotatable arm may be configured to rotate to move the first blade in an arc for tissue retraction. The second blade may be coupled to a distal end of the second rotatable arm. The second rotatable arm may be configured to rotate to move the second blade in an arc for tissue retraction. The third blade may be coupled to a distal end of the linearly translatable arm. The linearly translatable arm may be configured to translate to move the third blade in a line for tissue retraction. The first, second, and third blades may be configured to angulate to separate distal ends of the first, second, and third blades from one another for tissue retraction.

Another embodiment comprises a system for securing a retractor system to a patient's spine. The system may comprise a retractor blade comprising an interior blade surface, an exterior blade surface, and blade sides connecting the interior blade surface and the exterior blade surface. The system further may comprise a shim device comprising an interior shim surface, an exterior shim surface, and shim sides connecting the interior shim surface and the exterior shim surface. The shim sides each may extend outwardly from the exterior shim surface, wherein the shim device is configured to releasably couple to the retractor blade with the exterior shim surface facing the interior blade surface such that a distal tip of the shim device extends past a distal end of the retractor blade with the blade sides engaged in channels formed by the shim sides.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of the present invention and should not be used to limit or define the invention.

FIGS. 1 and 2 illustrate a retractor system in a closed configuration in accordance with one embodiment of the present technique.

FIGS. 3 and 4 illustrate a retractor system in an open configuration in accordance with one embodiment of the present invention.

FIG. 9 is a bottom view of a retractor frame in accordance with one embodiment of the present invention.

FIG. 10 is a cross-sectional view of a retractor frame in accordance with one embodiment of the present invention.

FIG. 14 is an exploded perspective view of a shim device and a retractor blade in accordance with one embodiment of the present invention.

FIG. 15 is a rear perspective view of a retractor blade in accordance with one embodiment of the present invention.

FIG. 18 is a perspective side view of a retractor blade in accordance with one embodiment of the present invention.

FIG. 19 is a close-up view taken along circle 233 of FIG. 18 in accordance with one embodiment of the present invention.

FIGS. 23 and 24 are perspective view showing installation of a shim device onto a retractor blade in accordance with one embodiment of the present invention.

DETAILED DESCRIPTION OF THE ILLUSTRATED EMBODIMENTS

Figure 5:
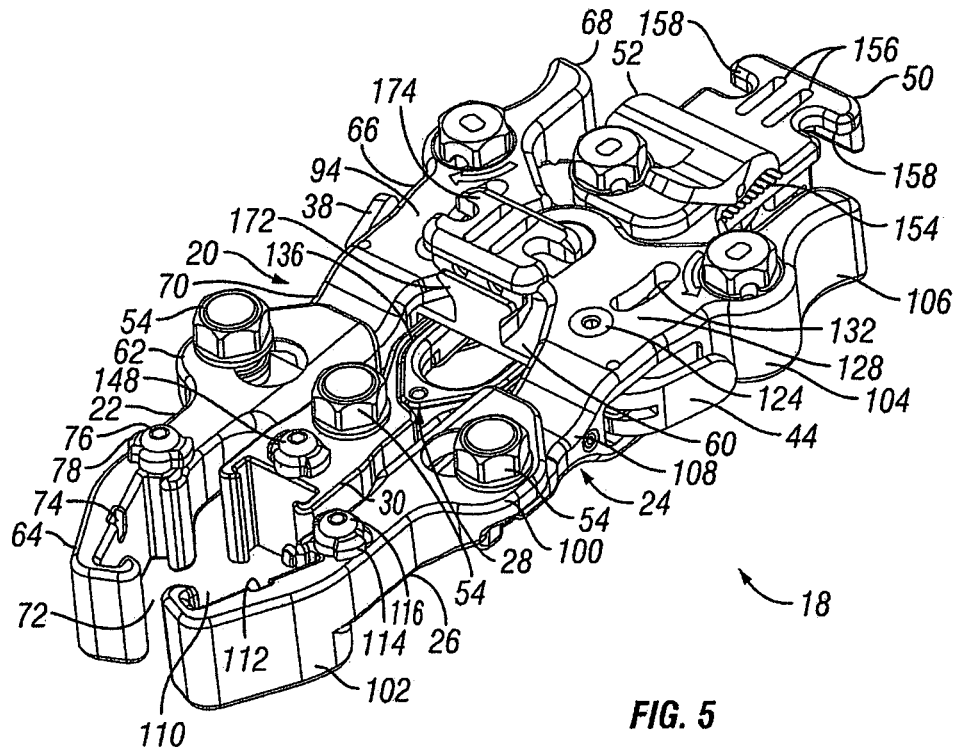
FIG. 5 illustrates a retractor frame in accordance with one embodiment of the present invention.
Figure 6:
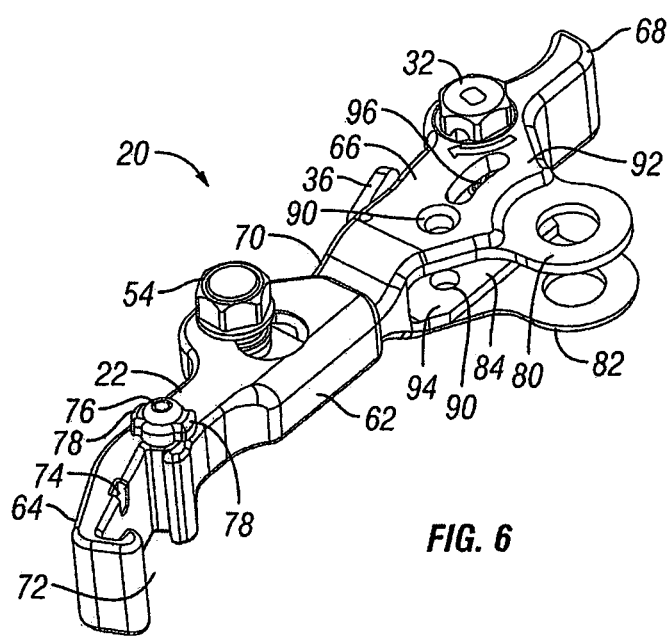
FIG. 6 illustrates a rotatable arm for use in a retractor system in accordance with one embodiment of the present invention.
Figure 7:
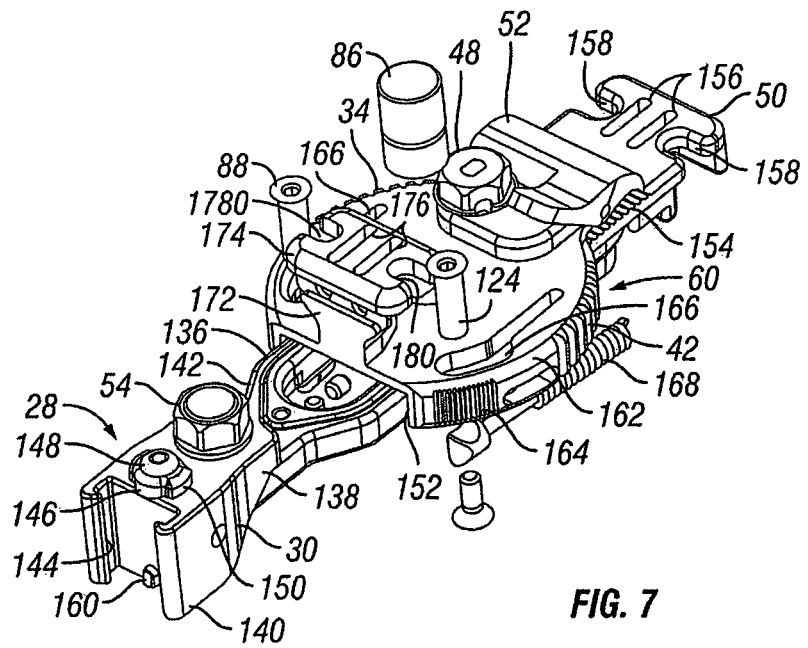
FIG. 7 illustrates a linearly translatable arm and a central gear housing for use in a retractor system in accordance with one embodiment of the present invention.
Figure 8:
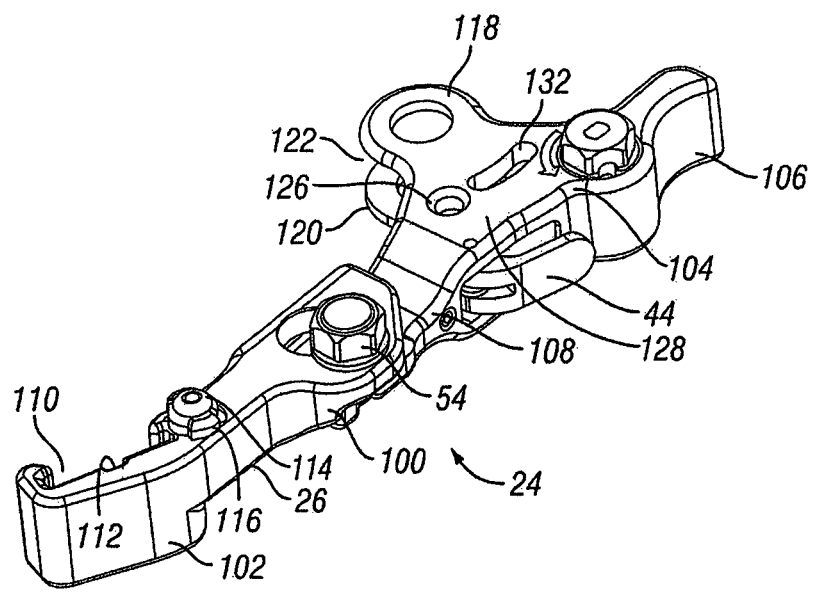
FIG. 8 illustrates a rotatable arm for use in a retractor system in accordance with one embodiment of the present invention.

FIGS. 1-4 illustrate a retractor system 10 that may be used to retract tissue in a surgical procedure in accordance with one embodiment of the present invention. The retractor system 10 comprises a first blade 12, a second blade 14, and a third blade 16. The first, second, and third blades 12, 14, 16 are each coupled to a retractor frame 18. The retractor frame 18 comprises a first rotatable arm 20 having a first blade attachment member 22 for holding and positioning the first blade 12. The retractor frame 18 further comprises a second rotatable arm 24 having a second blade attachment member 26 for holding and positioning the second blade 14. The retractor frame 18 further comprises a linearly translatable arm 28 having a third blade attachment member 30 for holding and positioning the third blade 16. The first and second rotatable arms 20, 24 and the linearly translatable arm 28 may be actuated so that the blades 12, 14, 16 may be separated a desired distance from each other. In addition, the blade attachment members 22, 26, and 30 may be actuated to angulate the blades 12, 14, 16, increasing the distance between the distal ends of the blades 12, 14, 16. In this manner, tissue surrounding an incision may be retracted providing access to the surgical site. In embodiments, the first, second, and third blades 12, 14, 16 may be individually actuated.

FIGS. 1-2 illustrate the retractor system 10 in a "closed" or non-retracted configuration, in accordance with one embodiment of the present invention. In the closed configuration, the first, second, and third blades 12, 14, 16 are radially disposed around a central bore 31 to form a substantially closed, tube-shaped structure.

FIGS. 3-4 illustrate the retractor system 10 in an "open" or retracted configuration, in accordance with one embodiment of the present invention. In the open configuration, the first, second, and third blades 12, 14, 16 have been moved so that they no longer form a tube-shaped structure that is substantially closed. Rather, the first and second blades 12, 14 have been rotated and angulated and third blade 16 has been linearly translated and angulated to enlarge the diameter of the central bore about which the blades 12, 14, 16 are arranged.

The first rotatable arm 20 may be actuated by rotation of an actuator 32. The actuator 32 may be a fastener, such as a hex screw (e.g., a 10 mm hex screw). The actuator 32 may be coupled to a planetary gear 180 (shown on FIG. 9) having teeth that engage a first sun gear 34. The engagement between the actuator 32, the planetary gear 180, and the first sun gear 34 may be described as a planetary gear mechanism in accordance with embodiments of the present invention. In the illustrated embodiments, a ratchet-locking mechanism 38 is included that engages teeth on the first sun gear 34. As the actuator 32 is turned, the first rotatable arm 20 should rotate as indicated by arrow 36 with the distal end of the arm 20 moving in an arc. For example, rotation of the actuator 32 in the counter-clockwise direction drives rotation of the first rotatable arm 20 as indicated by arrow 36 thereby rotating the first blade 12 in an arc away from the second and third blades 14, 16. In an embodiment, the first sun gear 34 is stationary with the planetary gear 180 rotating tooth by tooth along the first sun gear 34. In an embodiment, the ratchet-locking mechanism 38 engages the first sun gear 34 to prevent rotation of the first rotatable arm 20 in the counter-clockwise direction. The first rotatable arm 20 may be released from its rotated state (FIGS. 3-4) by depressing the lever of the ratchet-locking mechanism 38 to allow the first rotatable arm 20 to rotate back to its initial position (FIGS. 1-2).

In a similar manner to the first rotatable arm 20, the second rotatable arm 24 may be actuated by rotation of an actuator 40. The actuator 40 may be, for example, a fastener, such as a hex screw (e.g., a 10 mm hex screw). The actuator 40 may be coupled to a planetary gear 182 (shown on FIG. 9) having teeth that engage a second sun gear 42. The engagement between the actuator 40, the planetary gear 182, and the second sun gear 42 may be described as a planetary gear mechanism in accordance with embodiments of the present invention. It should be understood that use of the term "sun" is not meant to imply that the first and second sun gears 34, 42 are circular in shape but rather that the gears function in conjunction with the other components in a manner similar to what is commonly referred to as a planetary gear. In the illustrated embodiment, a ratchet-locking mechanism 44 is included that engages teeth on the second sun gear 42. As the actuator 40 is turned, the second rotatable arm 24 should rotate as indicated by arrow 46 with the distal end of the second rotatable arm 24 moving in an arc. For example, rotation of the actuator 40 in the counter-clockwise direction should drive rotation of the second rotatable arm 24 as indicated by arrow 46 thereby rotating the second blade 14 in an arc away from the first and third blades 12, 16. In an embodiment, the second sun gear 42 is stationary with the planetary gear 182 rotating tooth by tooth along the second sun gear 42. In an embodiment, the ratchet-locking mechanism 44 engages the second sun gear 42 to prevent rotation of the second rotatable arm 24 in the counter-clockwise direction. The second rotatable arm 24 may be released from its rotated state (FIGS. 3-4) by depressing the lever of the ratchet-locking mechanism 44 to allow the second rotatable arm 24 to rotate back to its initial position (FIGS. 1-2).

The linearly translatable arm 28 may be actuated by rotation of an actuator 48. The actuator 48 may be, for example, a fastener, such as a hex screw (e.g., a 10 mm hex screw). The actuator 48 may be coupled to a pinion gear (not shown) that engages teeth on rack portion 50 of the linearly translatable arm 28. As illustrated, the rack portion 50 may be on the opposite end of the linearly translatable arm 28 from the third blade attachment member 30. The engagement between the actuator 48, the pinion gear, and the rack portion 50 may be described as a rack and pinion gear mechanism in accordance with embodiments of the present invention. In the illustrated embodiment, ratchet-locking mechanism 52 is also included that engages teeth on the rack portion 50. As the actuator 48 is turned, the linearly translatable arm 28 moves in a line as illustrated in FIGS. 3-4. This will increase the distance between the third blade 16 and the first and second blades 12, 14. In an embodiment, the ratchet-locking mechanism 42 engages the rack portion 50 to prevent translation in the opposite direction that would shorten the distance between the blades 12, 14, 16. The linearly translatable arm 28 may be released from its translated state (FIGS. 3-4) by depressing the lever of the ratchet-locking mechanism 52 to allow the linearly translatable arm 28 to rotate back to its initial position (FIGS. 1-2) without having to turn the actuator 48.

In accordance with present embodiments, the first, second, and third blades 12, 14, 16 may be angulated by respective rotation of actuators 54. As used herein, angulation of the blades 12, 14, 16 refers to rotation of the distal ends of the blades 12, 14, 16 outwardly and upwardly, resulting in separation of the distal ends. The actuators 54 may be, for example, a fastener, such as a hex screws (e.g., 10 mm hex screws). As illustrated by FIGS. 3-4, each of the actuators 54 may be rotated to angulate the first, second, and third blades 12, 14, 16, respectively. As will be discussed in more detailed with respect to FIG. 13, rotation of the actuators 54 facilitates this angulation by angulating the blade attachment members 22, 26, 30 to cause corresponding angulation of the blades 12, 14, 16. In an embodiment, the angulation used is an infinite angle adjustment mechanism that is controlled by threading.

The first, second, and third blades 12, 14, 16 of the retractor system 10 may have one or more holes 58 extending through the blades 12, 14, 16 along their respective long axes. The holes 58 may be configured to allow passage of light components, k-wires, or other suitable instruments through the blades 12, 14, 16. The edges of the blades may be rounded, for example, to minimize the risk of damage to the retracted tissue. While illustrated with three blades, those of ordinary skill in the art will appreciate the retractor system 10 may include more, or less, than three blades configured to move as desired for a particular application. For example, a retractor system may be used that comprises four blades with two linearly translatable arms and two rotatable arms. Alternatively, a retractor may be used that comprises two rotatable arms or alternatively one linearly translatable arm and one rotatable arm.

It should be understood that the actuators 32, 40, 48, 54 may be configured to engage a variety of different tools to facilitate the desired rotation. For example, wrenches, screwdrivers, or any other suitable tools may be used to rotate the actuators 32, 40, 48, 54. In addition, while actuators 32, 40, 48, 54 are shown as fasteners, it should be understood that fasteners are not required to facilitate the movement. Other suitable devices, such as cranks, may be used to facilitate the desired movement.

An embodiment of the present invention includes using the retractor system 10 to retract tissue in a surgical procedure. For example, the retractor system 10 may be placed into an opening (e.g., an incision) in the patient's tissue with the retractor system 10 in the closed position. The surgeon (or other operator) may then separately rotate actuator 32 and actuator 40 to rotate the first rotatable arm 20 and the second rotatable arm 24, respectively, thus moving the first and second blades 12, 14 in an arc. The surgeon may also rotate actuator 48 to move the linearly translatable arm 28 and, thus, the third blade 16, in a line. In this manner, the first, second, and third blades 12, 14, 16 may be retracted (or spread) to provide enhanced access to the surgical site. To further enhance access, the surgeon may rotate each of actuators 54 to angulate the first, second, and third blades 12, 14, 16.

Turning now to FIGS. 5-11, the retractor frame 18 is illustrated in more detail in accordance with embodiments of the present invention. As previously mentioned, the retractor frame 18 may comprise a first rotatable arm 20, a second rotatable arm 24, and a linearly translatable arm 28. A portion of the second rotatable arm 24 is removed on FIG. 11 to illustrate interior components of the retractor frame 18. In addition, the retractor frame 18 may further comprise a central gear housing 60. As illustrated, the central gear housing 60 houses the first sun gear 34 and the second sun gear 42. In accordance with present embodiments, the first sun gear 34 and the second sun gear 42 are configured to facilitate rotation of the first rotatable arm 20 and the second rotatable arm 24, respectively.

The first rotatable arm 20 may comprise a first blade attachment member 22 having a proximal end 62 and a distal end 64. The first rotatable arm 20 may further comprise a base portion 66 having a proximal end 68 and a distal end 70. The proximal end 62 of the first blade attachment member 22 may be disposed over the distal end 70 of the base portion 66. The first blade attachment member 22 may be secured to the base portion 66 by a pivot pin (not shown). The distal end 64 of the first blade attachment member 22 may be configured to receive the first blade 12 (shown on FIGS. 1 and 3). For example, the distal end 64 may have a slot 72 that receives the first blade 12. A notch 74 in the distal end 64 may receive a corresponding protrusion in the first blade 12. Fastener 76 may secure the first blade 12 in the blade attachment member 22. As illustrated, the fastener 76 may include one or more radially extending protrusions 78. To secure the first blade 12, the first blade 12 may be inserted into slot 72 until the protruding portion of the blade 12 lands on the notch 74. The fastener 76 may be rotated until one of the protrusions 78 extends over the top of the first blade 12 to prevent its removal from the slot 72.

The base portion 66 may have a finger grip at the proximal end 68 that may be used to facilitate a controlled return of the first rotatable arm 20 after depression of the ratchet-locking mechanism 38. Top and bottom annular-shaped members 80, 82 may extend laterally from the first rotatable arm 22. Slot 84 may be formed in the first rotatable arm 20 for receiving the central gear housing 60. Pin 86 may extend through the annular-shaped members 80, 82 to secure the central gear housing 60 in the slot 84 with the teeth of the first sun gear 34 engaging the planetary gear 180. Set screw 87 should secure the pin 88 in the central gear housing 60. Pin 88 may extend through holes 90 in the upper and lower portions 92, 94 of the base portion 66. Pin 88 should be coupled to spring 170 for spring-loading the first rotatable arm 20. Upper slot 96 may be formed in the upper portion 92 of the base portion 66 to provide access to the central gear housing 60 and other components of the retractor frame 18. As illustrated by FIG. 9, there may be a corresponding lower slot 98 formed in the lower portion 94 of the base portion 66 that can provide access to the central gear housing 60 and other components of the retractor frame 18.

The second rotatable arm 24 may comprise a second blade attachment member 26 having a proximal end 100 and a distal end 102. The second rotatable arm 24 may further comprise a base portion 104 having a proximal end 106 and a distal end 108. The proximal end 100 of the second blade attachment member 26 may be disposed over the distal end 108 of the base portion 104. The second blade attachment member 26 may be secured to the base portion 104 by a pivot pin 105 (shown on FIG. 12). The distal end 102 of the second blade attachment member 26 may be configured to receive the second blade 14 (shown on FIGS. 1 and 3). For example, the distal end 102 may have a slot 110 that receives the second blade 14. A notch 112 in the distal end 102 may receive a corresponding protrusion in the second blade 14. Fastener 114 may secure the second blade 14 in the second attachment member 26. As illustrated, the fastener 114 may include one or more radially extending protrusions 116. To secure the second blade 14, it may be inserted into slot 110 until the protruding portion of the blade 14 lands on the notch 112. The fastener 114 may then be rotated until one of the protrusions 116 extends over the top of the second blade 14 to prevent its removal from the slot 110.

The base portion 104 may have a finger grip at the proximal end 106 that may be used to facilitate a controlled return of the second rotatable arm 24 after depression of the ratchet-locking mechanism 38. Top and bottom annular-shaped members 118, 120 may extend laterally from the second rotatable arm 26. Slot 122 may be formed in the second rotatable arm 24 for receiving the central gear housing 60. Pin 86 may extend through the annular-shaped members 118, 120 to secure the central gear housing 60 in the slot 122 with the teeth of the second sun gear 42 engaging the planetary gear 182. Pin 124 may extend through holes 126 in the upper and lower portions 128, 130 of the base portion 104. Pin 124 should be coupled to spring 168 for spring-loading the second rotatable arm 24. Upper slot 132 may be formed in the upper portion 128 of the base portion 104 to provide access to the central gear housing 60 and other components of the retractor frame 18. As illustrated by FIG. 9, there is a corresponding lower slot 134 formed in the lower portion 130 of the base portion 104 that can provide access to the central gear housing 60 and other components of the retractor frame 18.

The linearly translatable arm 28 may comprise a third blade attachment member 30 and a rack portion 50 separated from third blade attachment member 30 by a slotted middle portion 136. In an embodiment, the rack portion 50 may be at least partially slotted. The third blade attachment member 30 may have a proximal end 138 and distal end 140. The slotted middle portion 136 may comprise a distal end 142 on which the proximal end 138 of the third blade attachment member 30 may be disposed. A pin may secure the third blade attachment member 30 to the slotted middle portion 136. The distal end 140 of the third blade attachment member 30 may be configured to receive the third blade 16 (shown on FIGS. 1 and 3). For example, the distal end 140 may have a slot 144 that receives the third blade 16. A notch 146 in the distal end 140 may receive a corresponding protrusion in the third blade 16. Fastener 148 may secure the third blade 16 in the third blade attachment member 30. As illustrated, the fastener 148 may include one or more radially extending protrusions 150. To secure the third blade 16, it may be inserted into slot 144 until the protruding portion of the blade 16 lands on the notch 146. The fastener 148 may then be rotated until one of the protrusions 150 extends over the top of the third blade 16 to prevent its removal from the slot 144. A protrusion 160 in the bottom of the slot 144 may further secure the third blade 16 in the slot 144.

The slotted middle portion 136 may be coupled to the third blade attachment member 30 at its distal end 142 with the rack portion 50 on its other end. As illustrated, the slotted middle portion 136 may extend into a through passageway 152 in the central gear housing 60. The slotted middle portion 136 separates the rack portion 50 from the third blade attachment member 30. As illustrated, the rack portion 50 may extend from the through passageway 152 in the central gear housing 60. The rack portion 50 may further comprise rack teeth 153 that should engage with the actuator/pinion gear 48. Ratchet-locking mechanism 52 may further engage teeth 154 on the rack portion 50. The rack portion 50 may further comprise features for securing the retractor system 10 to an arm (not illustrated). Those of ordinary skill in the art should understand that the arm may be used to provide, for example, a connection between the retractor system 10 and an operating table. The features for securing the retractor system 10 to the arm may include, for example, a pair of slots 156 and semi-elliptical openings 158 on opposing sides of the rack portion 50.

The central gear housing 60 may comprise a first sun gear 34 on a first side and a second sun gear 42 on a second side. In the illustrated embodiment, the central gear housing 60 is generally disc shaped with a rim 162 about which the first sun gear 34 and the second sun gear 42 are individually rotatable. As illustrated, the rim 162 may further comprise teeth 164 that engage the ratchet-locking mechanism 44 of the second rotatable arm 24. While not illustrated, there may be corresponding teeth on the opposite side of the rim 162 for engaging the ratchet-locking mechanism 38 for the first rotatable arm 20. A central opening may be disposed in the central gear housing 60 through which pin 86 may be inserted. Central gear housing 60 may further comprise a through passageway 152 having a rectangular cross section. Central gear housing 60 may further comprise channels 166. In the illustrated embodiment, spring 170 may be coupled to pin 88 for providing the force to return the first rotatable arm 20 to its initial position when the ratchet-locking mechanism 38 is released. As further illustrated, pin 124 may be inserted into the other one of the channels 166. Spring 168 may be coupled to pin 124 for providing force to return the second rotatable arm 24 to its initial position when the ratchet-locking mechanism 44 is released. Central gear housing 60 may further comprise upwardly extending arm 172 to which arm attachment plate 174 may be attached. Arm attachment plate 174 may comprise features for attaching the retractor system 10 to a table connector, such as an arm. For example, arm attachment plate 174 may comprise slots 176 and semi-elliptical openings 178. As illustrated, ratchet-locking mechanism 52 may be coupled to the central gear housing 60 so as to engage teeth 154 on the rack portion 50 of the linearly translatable arm 28. As further illustrated, actuator 48 may extend through an opening in the central gear housing 60 so that a connected pinion gear (not illustrated) also engages the rack teeth 153.

Figure 12:
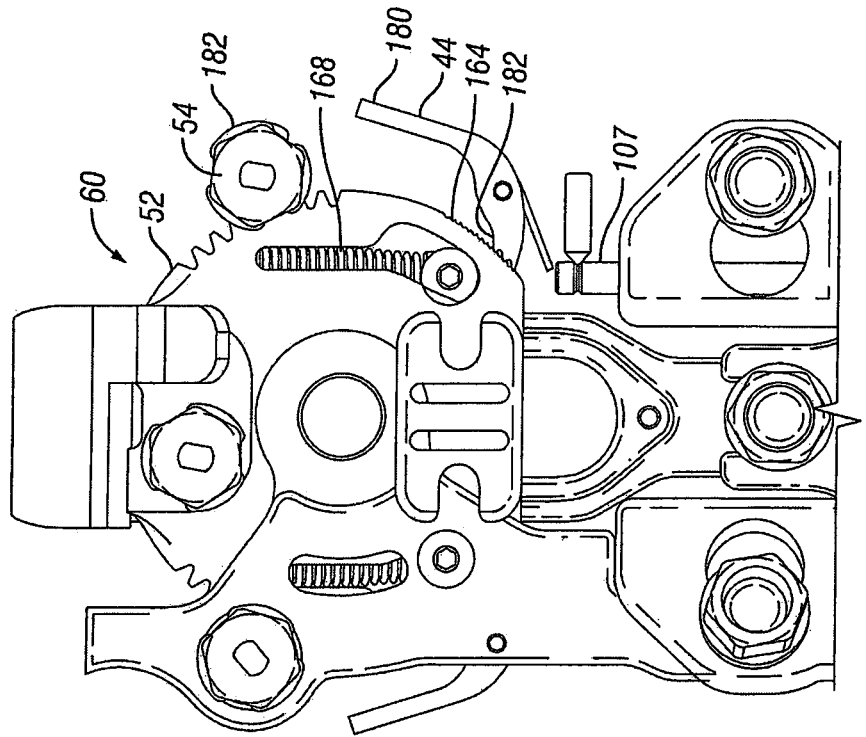
FIG. 12 illustrates a ratchet-locking mechanism in accordance with one embodiment of the present invention.
Figure 11:
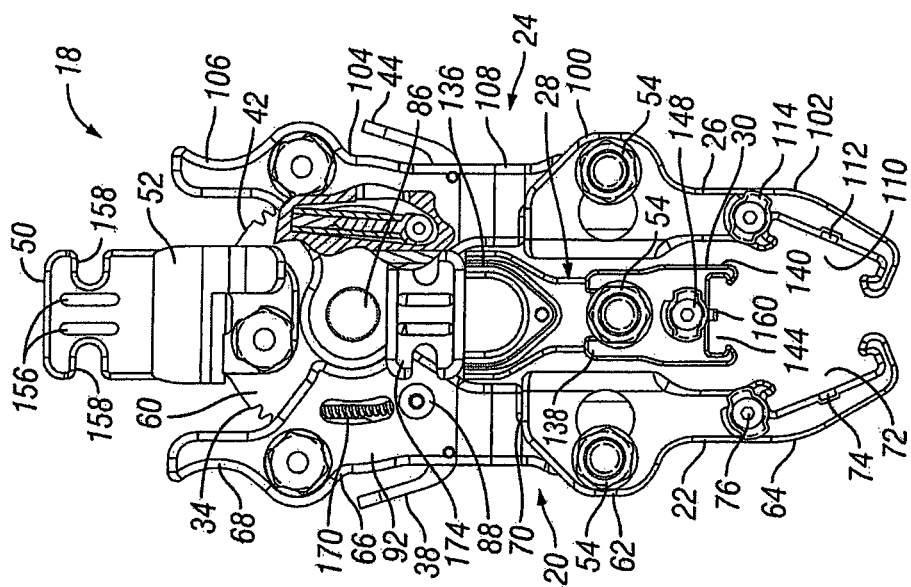
FIG. 11 is a top view of a retractor frame in accordance with one embodiment of the present invention.

FIG. 12 illustrates the ratchet-locking mechanism 44 in more detail in accordance with one embodiment of the present invention. In an embodiment, the ratchet-locking mechanism 44 includes a lever 180 and a nose 182. As illustrated, the nose 182 of the ratchet-locking mechanism 44 engages teeth 164 on the central gear housing 60. As previously discussed, rotation of the actuator 54 in the counter-clockwise direction should drive the planetary gear 182 tooth by tooth along the second sun gear 52. Rotation of the actuator 54 should drive corresponding rotation of the second rotatable arm 24 in the counter-clockwise direction. The nose 182 of the ratchet-locking mechanism 44 should engage the teeth 164 of the second sun gear 52 to allow movement of the second rotatable arm 24 in one direction, i.e., the counter-clockwise direction. The second rotatable arm 24 can be released from this rotated position by depressing the lever 180. The spring 168 should generally provide the force need to return the second rotatable arm 24 to its initial position when the lever 180 is released. While the previous discussion of FIG. 12 is with respect to the ratchet-locking mechanism 44, it should be understood that ratchet-locking mechanism 38 may be operated in a similar manner to restrict rotation of the first rotatable arm 20. It should further be noted that, while the previous discussion describes a ratchet-locking mechanism, other suitable devices for allowing movement of the rotatable arms in one direction may be used in accordance with the present invention.

Figure 13:
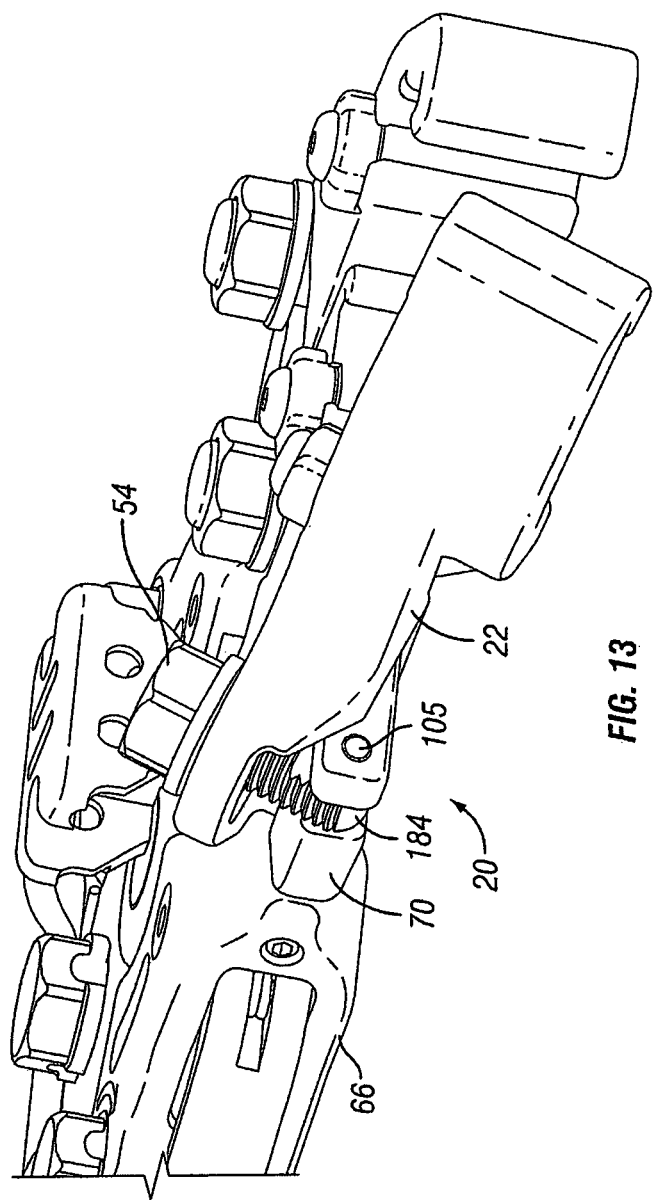
FIG. 13 illustrates angulation of a retractor blade in accordance with one embodiment of the present invention.

FIG. 13 describes angulation of the blade attachment member 22 in accordance with one embodiment of the present invention. As previously discussed, the first rotatable arm 20 comprises blade attachment member 22 coupled to the distal end 70 of the base portion 66. As illustrated, actuator 54 may secure the blade attachment member 22 onto the base portion 66. The actuator 54 may be threaded, for example, into a corresponding opening 184 in the base portion 66. The pin 107 (shown on FIG. 12) pivotally connects the attachment member 22 to the screw shaft of the actuator 54. A second pin 105 (shown on FIG. 13) connects the attachment member 22 through the base portion of the 66. The screw head of the actuator is provided with a portion that allows the attachment member to be retained within the head portion of the actuator and is pivotally rotatable when the actuator 54 is manipulated. The pin 107 and pin 105 create two separate axis of rotations. As the actuator is manipulated the attachment member 22 is rotated along the axis of rotation of pin 105. In an embodiment, the opening 184 may be angled, in that the axis of the opening 184 may be at an angle with respect to the z-axis of the first rotatable arm 20. Accordingly, as the actuator 54 is rotated, the blade attachment member 22 should pivot. In this manner, the blade attachment member 22 and, thus, the first blade 12 may be angulated. While the previous discussion of FIG. 12 and FIG. 13 is with respect to angulation of the first blade attachment member 22, it should be understood that second and third blade attachment members 26, 30 may be angulated in a similar manner. It should further be noted that, while the previous discussion describes an angled actuator for angulating the blade attachment member 22, 26, and 30, other suitable mechanisms for facilitating the desired blade angulation may be used in accordance with the present invention.

FIG. 14 illustrates a shim device 200 and a retractor blade 202 in accordance with one embodiment of the present invention. In an embodiment, the shim device 200 may be releasably coupled to the retractor blade 202. Those of ordinary skill in the art, with the benefit of this disclosure, should appreciate that the shim device 200 may be used, for example, to secure a retractor system 10 (shown on FIGS. 1-4) to a patient's spine. In an embodiment, the shim device 200 may be coupled to a retractor blade 202 secured to a retractor arm (such as linearly translatable arm 28 shown on FIGS. 1-4). In an embodiment, the shim device 200 may be coupled to the retractor blade 202 wherein a distal portion of the shim device 200 extends distally from the retractor blade 202 and into a patient's disc space 266 (shown on FIG. 24), securing the retractor system 10 to the spine. By securing the retractor system 10 to the spine, the retractor system 10 may be stabilized with less chance of moving from the intended target in embodiments of the present invention.

Those of ordinary skill in the art, with the benefit of this disclosure, will appreciate that the retractor blade 202 illustrated on FIG. 14 may be used with the retractor system 10 described above with respect to FIGS. 1-13 or with other retractor systems as desired for a particular application.

Figures 16, 17:
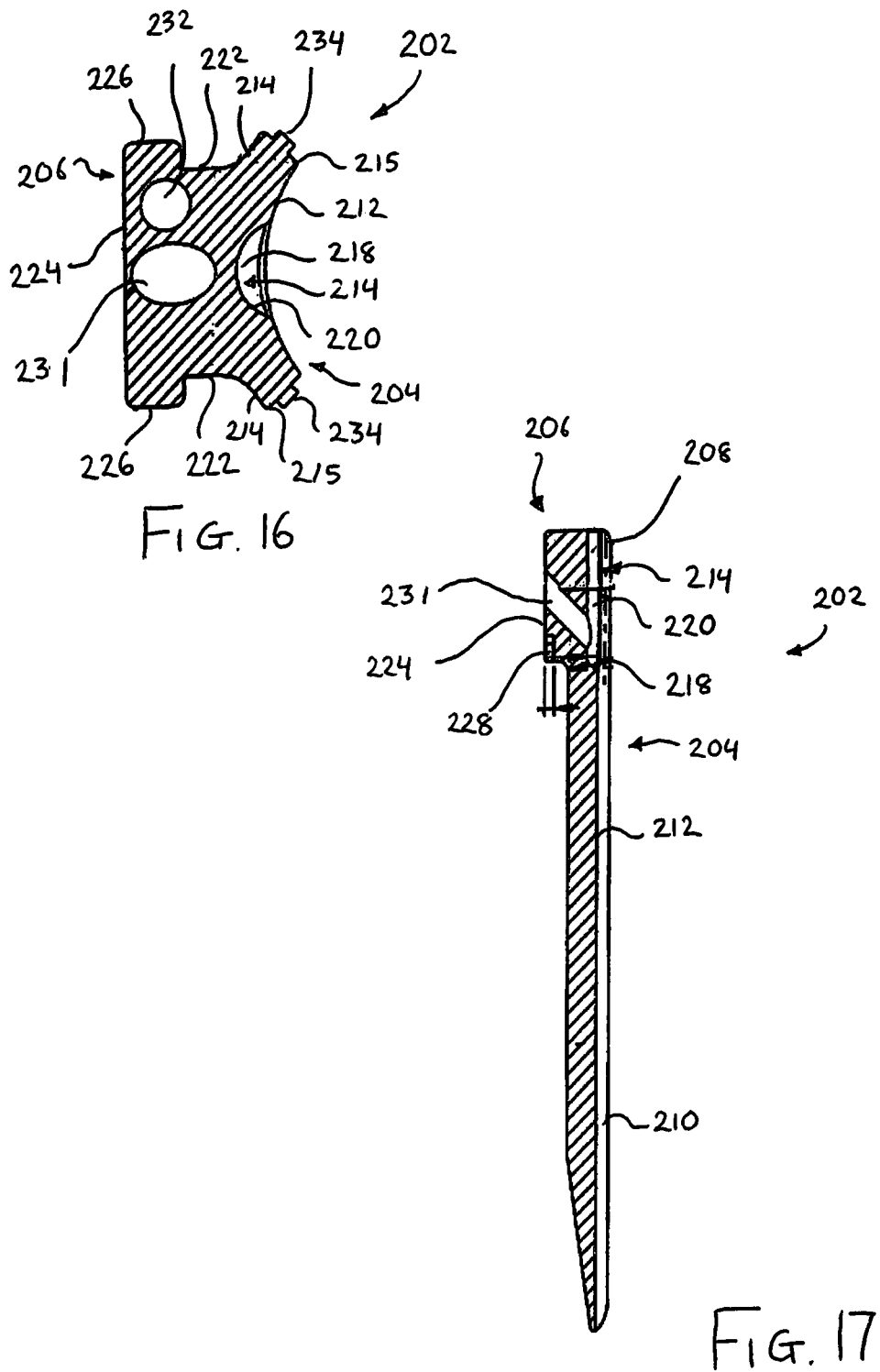
FIG. 16 is a cross-sectional top view of a retractor blade in accordance with one embodiment of the present invention.
FIG. 17 is a cross-sectional side view of a retractor blade in accordance with one embodiment of the present invention.

With additional reference to FIGS. 15-17, the retractor blade 202 will be described in more detail in accordance with one embodiment of the present invention. As illustrated, the retractor blade 202 may comprise a blade portion 204 and a retractor attachment portion 206 with the blade portion 204 having a proximal end 208 and a distal end 210. The blade portion 204 further may comprise an interior surface 212 and an exterior surface 214 with sides 215 connecting the interior surface 212 and the exterior surface 214. As best seen in FIG. 16, the interior surface 212 of the blade portion 204 may be generally curved concavely in accordance with one embodiment of the present invention. It is also contemplated that the interior surface 212 may be generally planar (not shown) in another embodiment. As illustrated, the interior surface 212 may have a channel 216 formed therein that extends longitudinally from the proximal end 208. A stop 218 (e.g., a seat) may be formed in the blade portion 204 at the distal end of the channel 216, i.e., the end of the channel 216 that is farthest from the proximal end 208 of the retractor blade 202. As will be discussed in more detail below, the stop 218 may engage the shim device 200 to prevent the shim device 200 from extending too far distally beyond the distal end 210 of the blade portion 204. In addition, the interior surface 212 may have a recessed surface 220 formed by the channel 216.

As illustrated by FIGS. 15-17, the retractor attachment portion 206 may be coupled to the proximal end 208 of the blade portion 204. As further illustrated, the retractor attachment portion 208 may project from the exterior surface 214 of the proximal end 208. In an embodiment, the retractor attachment portion 206 is integrally formed with the blade portion 204.

The retractor attachment portion 214 may have sides 222 and an exterior surface 224. In one embodiment, the exterior surface 224 of the retractor attachment portion 206 may be generally rectangular in shape. As illustrated, the sides 222 may extend from the proximal end 208 of the blade portion 204 with the exterior surface 224 of the retractor attachment portion 206 having overhanging sides 226. In one embodiment, the overhanging sides 226 project beyond the sides 222 of the retractor attachment portion 206. In the illustrated embodiment, the retractor attachment portion 206 includes a notch 228 in one end 230 of the exterior surface 224 for limiting the movement of the retractor blade 202 to the retractor frame 18. In one embodiment, the retractor blade 202 may be secured to the linearly translatable arm 28. To limit movement of the retractor blade 202, it may be inserted into slot 144 until the notch 228 engages the protrusion 160 in the bottom of the slot 144 to prevent further movement of the retractor blade 202 in the slot 144. The retractor attachment portion 206 further may comprise one or more holes 232 extending there through. The holes 232 may be configured to allow, for example, passage of light components, k-wires, or other suitable instruments through the retractor blade 202.

As best seen in FIGS. 15-17, the retractor blade 202 may further include a through bore 231. In the illustrated embodiment, the through bore 231 extends from the exterior surface 224 of the retractor attachment portion 206 to the interior surface 212 of the blade portion 204. In one embodiment, the through bore 231 extends through the retractor blade 202 at an oblique angle with respect to the longitudinal axis of the retractor blade 202. The through bore 231 may be configured to receive a tool for removing the retractor blade 202 from the retractor system 10, for example. With reference to FIGS. 18 and 19, the blade portion 204 of the retractor blade 202 may further comprise one or more locking tabs 234. As will be discussed in more detail below the locking tabs 234 may be configured to engage shim device 200 preventing the shim device 200 from, for example, backing out of the disc space 266 (shown on FIG. 24) during a surgical procedure. In other words, the locking tabs 234 may be configured to lock the shim device 200 onto the retractor blade 202. The blade portion 204 may comprise two locking tabs 234, in one embodiment, with each of the locking tabs 234 protruding from one of the sides 215 of the blade portion 204. In the illustrated embodiment, the locking tabs 234 are located above the stop 218 that is formed at the distal end of the channel 216 in the interior surface 212 of the blade portion 204. As best seen in FIG. 19, the locking tabs 234 may have an exterior surface 236. In an embodiment, at least a portion of the exterior surface 236 is ramped.

In another embodiment, as best seen in FIG. 18A, surface 212 may not have a channel 216 or stop 218. Instead, retractor blade 202 may include one or more additional locking tabs 235 located distally of locking tabs 234. Locking tabs 235 provide the same function as stop 218, namely, locking tabs 235 may engage the shim device 200 to prevent the shim device 200 from extending too far distally beyond the distal end 210 of the blade portion 204. The locking tabs 235 may have an exterior surface 237. In an embodiment, at least a portion of the exterior surface 237 is ramped.

Figure 20:
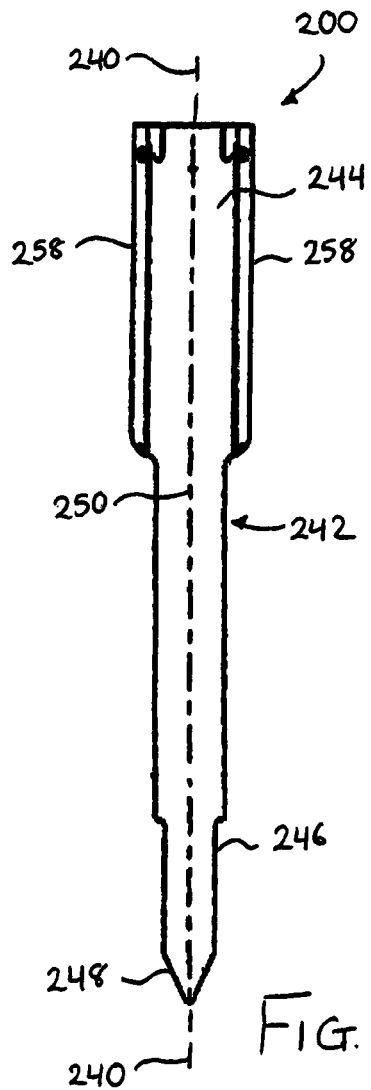
FIG. 20 is a front view of a shim device in accordance with one embodiment of the present invention.
Figure 21:
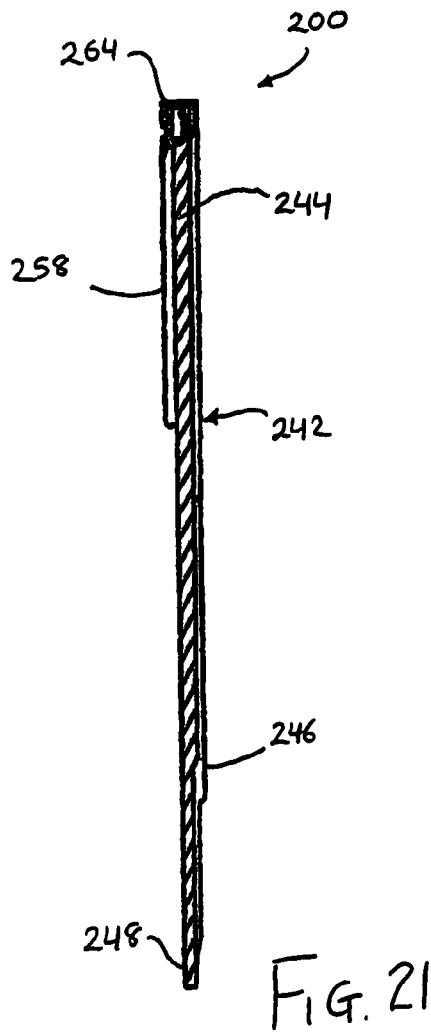
FIG. 21 is a cross-sectional side view of a shim device in accordance with one embodiment of the present invention.
Figure 22:
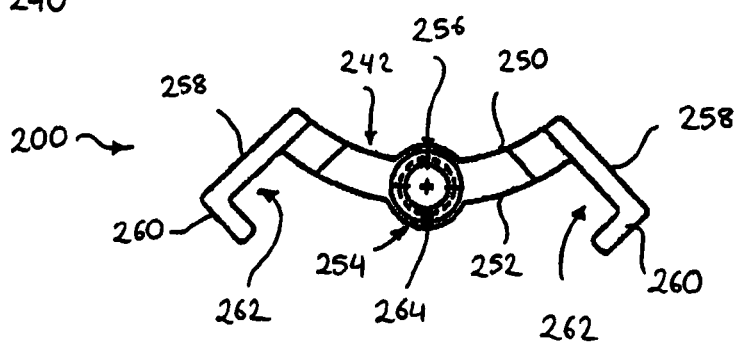
FIG. 22 is a top end view of a shim device in accordance with one embodiment of the present invention.

Referring now to FIGS. 14 and 20-22, the shim device 200 will be described in more detail in accordance with one embodiment of the present invention. FIG. 21 is a cross-sectional view of the shim device 200 taken along line 240 of FIG. 20. As illustrated, the shim device 200 includes a shim portion 242 having a proximal end 244 and a distal end 246. A distal tip 248 may be formed at the distal end 246 of the shim portion 242 in one embodiment. The shim portion 242 further may comprise an interior surface 250 and an exterior surface 252. As best seen in FIG. 22, The interior surface 250 of the shim portion 242 may be generally curved concavely, and the exterior surface 252 of the shim portion 242 may be generally curved convexly, in accordance with one embodiment of the present invention. It is also contemplated that the interior surface 250 and/or the exterior surface 252 may be generally planar (not shown) in another embodiment. As illustrated, the exterior surface 252 may have a protruding portion 254 that extends out from the exterior surface 252 and lengthwise from the proximal end 244. The protruding portion 254 should only extend a portion of the length of the shim portion 242. In one embodiment, the protruding portion 254 may be generally curved convexly. The protruding portion 254 may be dimensioned to engage with the channel 216 formed in the interior surface 212 of the retractor blade 202. In another embodiment, the protruding portion 254 may abut and rest against the interior surface 212 of the retractor blade 202. As will be disclosed in more detail below, in one embodiment, the lower end of the protruding portion 254 should engage the stop 218 in the retractor blade 202 to prevent the shim device 200 from extending too far beyond the distal end 210 of the retractor blade 202 (shown on FIGS. 25 and 26). In another embodiment, retractor blade 202 may include one or more additional locking tabs 235 located distally of locking tabs 234 instead of channel 216 with stop 218. Locking tabs 235 provide the same function as stop 218, namely, locking tabs 235 may engage the shim device 200 to prevent the shim device 200 from extending too far distally beyond the distal end 210 of the blade portion 204. In one embodiment, a second protruding portion 256 is formed in the exterior surface 250 of the shim portion 242.

As further illustrated, the shim device 200 may further include sides 258. In the illustrated embodiment, the sides 258 each extend transversely from the shim portion 242. As best seen in FIGS. 20 and 21, the sides 258 each also have a length and extend along a portion of the length of the shim portion 242. In one embodiment, the end of the sides 258 is bent whereby a bent end 260 is formed that extends, for example, at an angle of approximately 90° from the remainder of the sides 258. As illustrated, channels 262 may be formed in the shim device 200 by the bent end 260. As will be discussed in more detail below, the sides 258 of the shim device 200 wrap around the sides 215 of the retractor blade 202 (shown on FIG. 25), holding the shim device 200 in place.

With reference to FIGS. 21 and 22, a hole 264 may be formed in the shim device 200. In the illustrated embodiment, the hole 264 is a blind hole as it does not extend all the way through the shim device 200. In one embodiment (not shown), the hole 264 may be threaded to, for example, receive a tool. As illustrated, the hole 200 may be formed in the proximal end 244 of the shim portion 242 and extend longitudinally into the shim portion 242. As will be discussed in more detail below with respect to FIG. 27, a tool may be configured to engage the hole 200 and, for example, outwardly displace the sides 258, releasing the locking engagement between the locking tabs 234 (shown on FIG. 19) and the sides 258.

Figure 25:
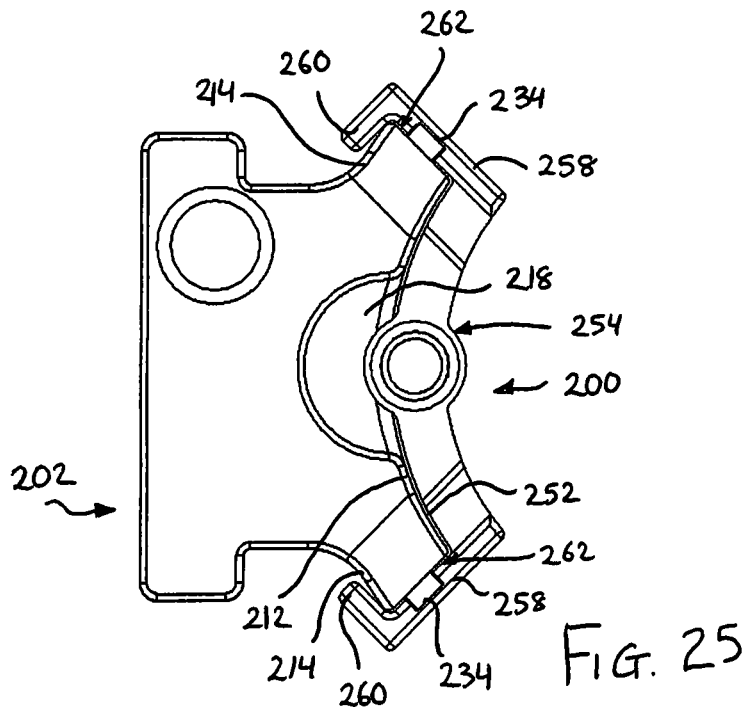
FIG. 25 is a top end view of a shim device disposed on a retractor blade in a locked configuration in accordance with one embodiment of the present invention.
Figure 26:
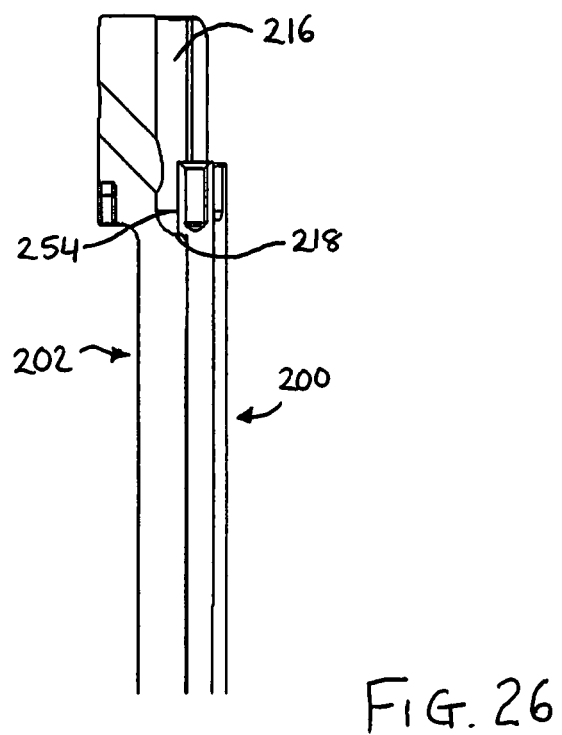
FIG. 26 is a cross-sectional view of a shim device installed on a retractor blade in accordance with one embodiment of the present invention.

Turning now to FIGS. 23-26, mounting of the shim device 200 onto the retractor blade 202 will be described in accordance with one embodiment of the present invention. As illustrated by FIG. 23, the shim device 200 should be placed such that the maximum length of the shim device 200 extends generally parallel to the maximum length of the retractor blade 202 with the proximal end 244 of the shim device 200 extending beyond the proximal end 208 of the retractor blade 202. The shim device 200 may then be slid onto the retractor blade 202 with the exterior surface 252 of the shim device 200 facing the interior surface 212 of the retractor blade 202 such that the sides 262 of the shim device 200 engage the sides 215 of the retractor blade 202. In one embodiment, the sides 262 of the shim device 200 wrap around the sides 215 of the retractor blade 202 with the bent end 260 holding the retractor blade 202 in an engaged position, as best seen in FIG. 25. In this manner, the sides 215 of the retractor blade 202 ride in the channel 262 formed in the shim device 200 by the sides 262. The shim device 200 may then be slid further down the retractor blade 202 such that the distal tip 246 of the shim device 200 extends distally beyond the distal end 210 of the retractor blade 202 and into an extended position, as best seen in FIG. 24. In the illustrated embodiment, the distal tip 246 penetrates a spinal disc 266 securing the retractor blade 202 to the patient's spine. As previously mentioned, a stop 218 may be formed at the distal end of the channel 216 in the retractor blade 202, in certain embodiments. As best seen in FIGS. 25 and 26, the protruding portion 254 of the shim device 200 may engage stop 218 to prevent the distal tip 246 of the shim device 200 from extending too far beyond the distal end 210 of the retractor blade 202.

In another embodiment, as best seen in FIG. 18A, surface 212 may not have a channel 216 or stop 218. Instead, retractor blade 202 may include one or more additional locking tabs 235 located distally of locking tabs 234. Locking tabs 235 provide the same function as stop 218, namely, locking tabs 235 may engage the shim device 200 by abutting the sides 258 to prevent the shim device 200 from extending too far distally beyond the distal end 210 of the blade portion 204.

Figure 27:
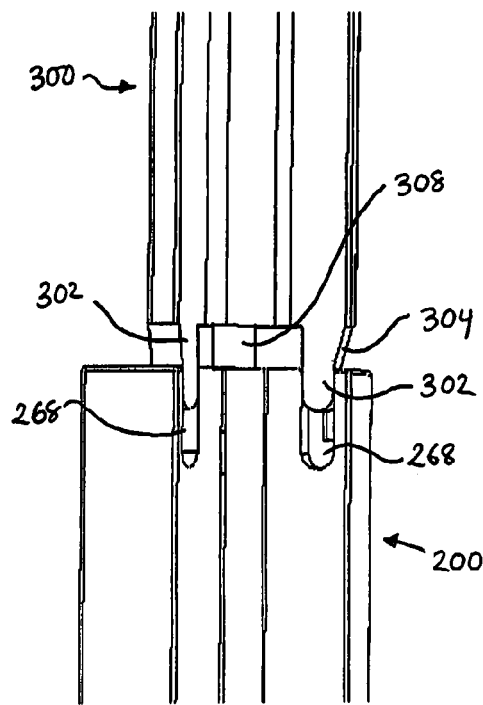
FIGS. 27 and 28 are close-up perspective views illustrating use of a tool for removal of the shim device from the retractor blade.
Figure 28:
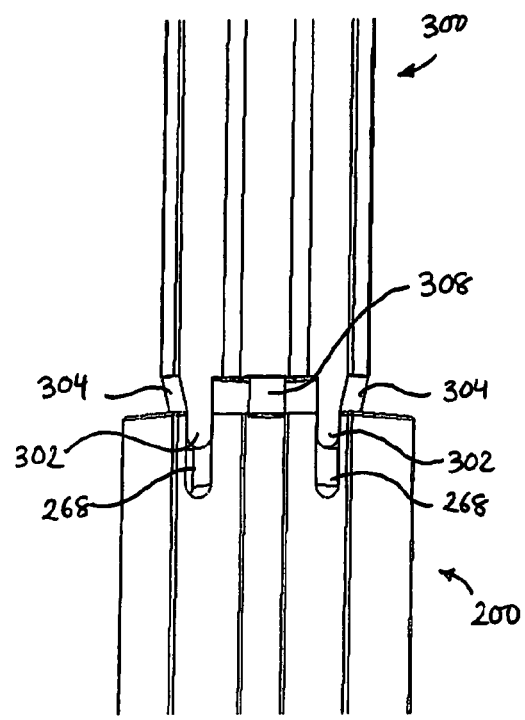

As previously mentioned, the retractor blade 202 may contain locking tabs 234 for preventing proximal removal of the shim device 200 after extension in accordance with one embodiment of the present invention. As the shim device 200 is slid down the retractor blade 202, the locking tabs 234 on the sides 215 of the retractor blade 202 should engage the sides 258 of the shim device 200. Because the locking tabs 234 are ramped (shown on FIG. 19), in one example, axial force applied to the shim device 200 may force the shim device 200 over the locking tabs 234 and into an extended position, as best seen in FIG. 25. As best seen in FIGS. 27 and 28, in one embodiment, a tool 300 may be used to engage the shim device 200 and displace the sides 258 outwardly such that the sides 258 of the shim device 200 can be slid past the locking tabs 234. In one particular embodiment, one or more slots 268 may provided at the proximal end 244 of the shim device 200 that allow the sides 258 to be displaced outwardly. The locking tabs 234 should prevent the distal tip 246 of the shim device 200 from moving back towards the distal end 210 of the retractor blade 202 once the shim device 200 is slid past the locking tabs 234. In this manner, the distal tip 246 of the shim device 200 should be prevented backing out of the spinal disc 266, so long as the retractor blade 202 remains in a fixed position.

With reference to FIGS. 27 and 28, to remove the shim device 200 from the retractor blade 202, a tool 300 may be used, in one embodiment, to engage the shim device 200 and displace the sides 258 outwardly. In one embodiment, the tool 300 may include engagement members 302 that include ramped surfaces 304 as well as a central shaft 308 that may be threaded. Tool 300 engages shim device 200 by having central shaft 308 threadingly engage hole 264 on the shim device 200. As the tool 300 advances, the engagement members 302 engage the slots 268 with the ramped surfaces riding against the sides of the slots 268. This causes the sides to displace outwardly. With the sides 258 displaced outwardly, the shim device 200 may slid proximally along retractor blade 202 until the shim device 200 is removed from the retractor blade 202.

While it is apparent that the invention disclosed herein is well calculated to fulfill the objects stated above, it will be appreciated that numerous modifications and embodiments may be devised by those skilled in the art. Although individual embodiments are discussed, the invention covers all combinations of all those embodiments.

What is claimed is:

1. A retractor system comprising:
   a retractor frame comprising a first arm, a second arm, and a third arm coupled to the first arm and second arm;
   a first blade coupled to a distal end of the first arm;
   a second blade coupled to a distal end of the second arm;
   a third blade coupled to a distal end of the third arm, the third blade comprising an interior blade surface, an exterior blade surface, and blade sides connecting the interior blade surface and the exterior blade surface;
   a first planetary gear mechanism coupled to the first arm for rotating the first arm;
   a second planetary gear mechanism coupled to the second arm for rotating the second arm; and
   a shim device comprising an interior shim surface, an exterior shim surface, and shim sides connecting the interior shim surface and the exterior shim surface, wherein the shim sides each extend outwardly from the exterior shim surface,
   wherein the shim device is configured to releasably couple to the retractor blade with the exterior shim surface facing the interior blade surface,
   wherein the shim device at least partially wraps around the retractor blade from the interior blade surface to the exterior blade surface when the shim device is releasably coupled to the retractor blade, and
   wherein the first arm is configured to rotate to move the first blade in an arc for tissue retraction, wherein the second arm is configured to rotate to move the second blade in an arc for tissue retraction, and wherein the third arm is configured to linearly translate to move the third blade in a line for tissue retraction.

2. The retractor system of claim 1, wherein the first, second, and third blades are each configured to angulate to separate distal ends of the first, second, and third blades from one another for tissue retraction.

3. The retractor system of claim 1 further comprising a rack and pinion gear mechanism for translating the third arm in a line.

4. The retractor system of claim 1, wherein the blade sides each comprise a locking tab configured to restrict movement of the distal tip of the shim device towards the distal end of the third blade when the shim device and the third blade are releasably coupled.

5. The retractor system of claim 1, wherein the interior blade surface comprises a seat extending there from configured to restrict movement of the distal tip of the shim device away from the third blade when the shim device and the third blade are releasably coupled.

6. The retractor system of claim 5, wherein the exterior shim surface has a protruding portion configured to engage the seat when the shim device and the third blade are releasably coupled.

* * * * *